United States Patent [19]

Berger et al.

[11] 4,009,181

[45] Feb. 22, 1977

[54] CYCLOPENTA[b]INDOLE-2-CARBOXYLIC ACIDS AND DERIVATIVES THEREOF

[75] Inventors: Leo Berger, Montclair; Alfred John Corraz, Wayne, both of N.J.

[73] Assignee: Hoffmann-La Roche Inc., Nutley, N.J.

[22] Filed: Dec. 12, 1974

[21] Appl. No.: 532,112

Related U.S. Application Data

[60] Division of Ser. No. 325,764, Jan. 22, 1973, Pat. No. 3,868,387, which is a continuation of Ser. No. 133,738, April 15, 1971, abandoned, which is a continuation-in-part of Ser. No. 40,443, May 25, 1970, abandoned.

[52] U.S. Cl. .......................................... 260/326.27

[51] Int. Cl.[2] ....................................... C07D 209/70

[58] Field of Search .................... 260/313.1, 326.27

[56] References Cited

UNITED STATES PATENTS

| | | | |
|---|---|---|---|
| 3,535,326 | 10/1970 | Yamamoto et al. | 260/315 |
| 3,655,697 | 4/1972 | Shen et al. | 260/315 |
| 3,824,314 | 7/1974 | Lacoume | 260/315 |

*Primary Examiner*—Paul M. Coughlan, Jr.

*Attorney, Agent, or Firm*—Samuel L. Welt; Bernard S. Leon; William G. Isgro

[57] ABSTRACT

1,2,3,4-Tetrahydrocarbazoles and cyclopenta[b]indoles prepared from the corresponding phenyl hydrazines and corresponding cyclohexanones or cyclopentanones, respectively, are described. The products of the invention are useful anti-inflammatory, analgesic and anti-rheumatic agents.

2 Claims, No Drawings

CYCLOPENTA[b]INDOLE-2-CARBOXYLIC ACIDS AND DERIVATIVES THEREOF

CROSS-REFERENCE TO RELATED APPLICATIONS

This application is a division of U.S. patent application Ser. No. 325,764, filed Jan. 22, 1973, U.S. Pat. No. 3,868,387, which in turn is a continuation of U.S. patent application Ser. No. 133,738, filed Apr. 15, 1971, now abandoned, which in turn is a continuation-in-part of U.S. patent application Ser. No. 40,433, filed May 25, 1970, now abandoned.

BRIEF SUMMARY OF THE INVENTION

The invention relates to compounds of the formula

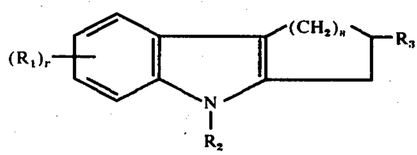

wherein $n$ and $r$ are independently 1 or 2; $R_1$ is hydrogen, halogen, hydroxy, cyano, lower alkyl, lower alkoxy, benzyloxy, lower alkylthio, trifluoromethyl, carboxy, carbo-lower alkoxy, nitro, amino, mono-lower alkylamino, di-lower alkylamino, sulfamoyl, di-lower alkylsulfamoyl or difluoromethylsulfonyl, and when $r$ is 2, $R_1$ with an adjacent $R_1$ is also lower alkylenedioxy; $R_2$ is hydrogen, lower alkyl, acyl, halo-substituted acyl, aralkyl or halo-aralkyl; and $R_3$ is

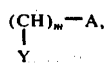

wherein A is cyano, hydroxy or lower alkoxy, Y is hydrogen or methyl, and $m$ is 0 to 7, or

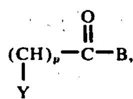

wherein B is hydroxy, carboxy, lower alkyl, lower alkoxy, amino, mono-lower alkylamino, di-lower alkylamino, amino-lower alkoxy, mono-lower alkylamino-lower alkoxy, di-lower alkylamino-lower alkoxy, Y is hydrogen or methyl and $p$ is 0 to 7, provided that when $n$ is 2 and $R_3$ is —COOH, at least one of $R_1$ or $R_2$ must be other than hydrogen, and provided that when $R_2$ is acyl or halo-substituted acyl, $R_1$ must be other than hydrogen or lower alkoxy, their enantiomers, and when $R_1$ is carboxy and/or when B is hydroxy or carboxy, salts thereof with pharmaceutically acceptable bases, and when $R_1$ is amino, mono-lower alkylamino or di-lower alkylamino, and/or when B is amino-lower alkoxy, mono-lower alkylamino-lower alkoxy or di-lower alkylamino-lower alkoxy, addition salts thereof with pharmaceutically acceptable acids.

The end products are useful as anti-inflammatory, analgesic and anti-rheumatic agents.

DETAILED DESCRIPTION OF THE INVENTION

As used herein, the term "lower alkyl" denotes a straight or branched chain hydrocarbon group containing 1–7 carbon atoms, for example, methyl, ethyl, propyl, isopropyl, butyl, isobutyl, tertiary butyl, neopentyl, pentyl, heptyl, and the like. The term "lower alkoxy" denotes an alkyl ether group in which the alkyl group is as described above, for example, methoxy, ethoxy, propoxy, isopropoxy, butoxy, pentoxy and the like. The term "halogen" denotes all the halogens; that is, bromine, chlorine, fluorine and iodine; bromine and chlorine are preferred. The term "aryl" denotes phenyl or phenyl bearing one or more substituents selected from the group consisting of halogen, trifluoromethyl, lower alkyl, lower alkoxy, nitro, amino, lower alkylamino and di-lower alkylamino. The term "aralkyl" as used herein denotes a straight or branched chain lower alkyl group in which one or more of the hydrogen atoms have been replaced by an aryl group. The term "acyl" denotes an "alkanoyl" group derived from an aliphatic carboxylic acid of 1 to 7 carbon atoms, for example, formyl, acetyl, propionyl, and the like, and an "aroyl" group derived from an aromatic carboxylic acid, such as benzoyl and the like. The term "lower alkylenedioxy" preferably denotes methylenedioxy and the like.

Exemplary of mono-lower alkylamino are methylamino, ethylamino and the like. Exemplary of di-lower alkylamino are dimethylamino, diethylamino and the like. Exemplary of amino-lower alkoxy are aminomethoxy, aminoethoxy and the like. Exemplary of mono-lower alkylamino-lower alkoxy are methylamino-methoxy, ethylaminoethoxy and the like. Exemplary of di-lower alkylamino-lower alkoxy are dimethylaminomethoxy, diethylaminoethoxy and the like. Exemplary of di-lower alkylsulfamoyl are dimethylsulfamoyl, diethylsulfamoyl and the like.

The invention relates to compounds of the formula

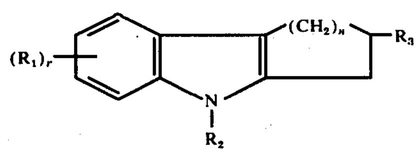

wherein $n$ and $r$ are independently 1 or 2; $R_1$ is hydrogen, halogen, hydroxy, cyano, lower alkyl, lower alkoxy, benzyloxy, lower alkylthio, trifluoromethyl, carboxy, carbo-lower alkoxy, nitro, amino, mono-lower alkylamino, di-lower alkylamino, sulfamoyl, di-lower alkylsulfamoyl or difluoromethylsulfonyl, and when $r$ is 2, $R_1$ with an adjacent $R_1$ is also lower alkylenedioxy; $R_2$ is hydrogen, lower alkyl, acyl, halo-substituted acyl, aralkyl or halo-aralkyl; $R_3$ is

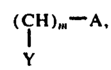

wherein A is cyano, hydroxy or lower alkoxy, Y is hydrogen or methyl, and $m$ is 0 to 7, or

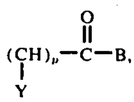

wherein B is hydroxy, carboxy, lower alkyl, lower alkoxy, amino, mono-lower alkylamino, di-lower alkylamino, amino-lower alkoxy, mono-lower alkylamino-lower alkoxy, or di-lower alkylamino-lower alkoxy, Y is hydrogen or methyl and $p$ is 0 to 7, provided that when $n$ is 2 and $R_3$ is —COOH, at least one of $R_1$ or $R_2$ must be other than hydrogen, and provided that when $R_2$ is acyl or halo-substituted acyl, $R_1$ must be other than hydrogen or lower alkoxy,
their enantiomers, and when $R_1$ is carboxy and/or when B is hydroxy or carboxy, salts thereof with pharmaceutically acceptable bases, and when $R_1$ is amino, mono-lower alkylamino or di-lower alkylamino, and/or when B is amino-lower alkoxy, mono-lower alkylamino-lower alkoxy or di-lower alkylamino-lower alkoxy, addition salts thereof with pharmaceutically acceptable acids.

A preferred subgenus of the compounds of formula I is characterized by the formula

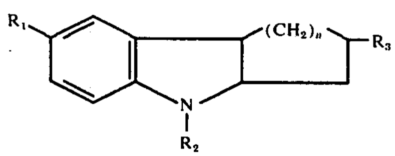

wherein $R_1$, $R_2$, $R_3$ and n are as previously described, their enantiomers, and the respective salts thereof as herein described.

Preferred compounds of formula I wherein n is 1 have the formula

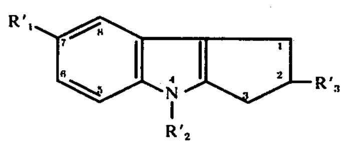

wherein $R'_1$ is halogen, lower alkyl or lower alkoxy; $R'_2$ is hydrogen and $R'_3$ is carboxy, their enantiomers, and salts thereof with pharmaceutically acceptable bases.

Preferred compounds of formula I wherein n is 2 have the formula

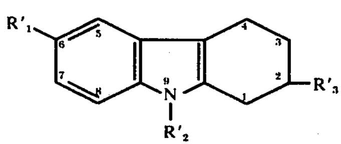

wherein $R'_1$ is halogen, lower alkyl or lower alkoxy; $R'_2$ is hydrogen and $R'_3$ is carboxy, their enantiomers, and salts thereof with pharmaceutically acceptable bases.

Preferred compounds of formula Ia' are 7-chlorocyclopenta [b]indole-2-carboxylic acid, 7-methylcyclopenta[b]indole-2-carboxylic acid and 7-methoxycyclopenta[b]indole-2-carboxylic acid.

Preferred compounds of formula Ib' are 6-chloro-1,2,3,4-tetrahydrocarbazole-2-carboxylic acid, 6-methyl-1,2,3,4-tetrahydrocarbazole-2-carboxylic acid and 6-methoxy-1,2,3,4-tetrahydrocarbazole-2-carboxylic acid.

Examples of compounds of this invention corresponding to formula I wherein $n$ is 2 are:

6-chloro-1,2,3,4-tetrahydrocarbazole-2-carboxylic acid;
6-chloro-1,2,3,4-tetrahydrocarbazole-2-carboxylic acid ethyl ester;
6-methyl-1,2,3,4-tetrahydrocarbazole-2-carboxylic acid;
6-methoxy-1,2,3,4-tetrahydrocarbazole-2-carboxylic acid;
9-(4-chlorobenzyl)-6-methoxy-1,2,3,4-tetrahydrocarbazole-2-carboxylic acid;
6-nitro-1,2,3,4-tetrahydrocarbazole-2-carboxylic acid;
7-chloro-1,2,3,4-tetrahydrocarbazole-2-carboxylic acid;
7-methyl-1,2,3,4-tetrahydrocarbazole-2-carboxylic acid;
8-chloro-1,2,3,4-tetrahydrocarbazole-2-carboxylic acid;
6-fluoro-1,2,3,4-tetrahydrocarbazole-2-carboxylic acid;
6-bromo-1,2,3,4-tetrahydrocarbazole-2-carboxylic acid;
6,7-dichloro-1,2,3,4-tetrahydrocarbazole-2-carboxylic acid;
5,6-dichloro-1,2,3,4-tetrahydrocarbazole-2-carboxylic acid;
6-trifluoromethyl-1,2,3,4-tetrahydrocarbazole-2-carboxylic acid;
6-chloro-7-methyl-1,2,3,4-tetrahydrocarbazole-2-carboxylic acid;
6-chloro-5-methyl-1,2,3,4-tetrahydrocarbazole-2-carboxylic acid;
9-methyl-1,2,3,4-tetrahydrocarbazole-2-carboxylic acid;
7,8-dichloro-1,2,3,4-tetrahydrocarbazole-2-carboxylic acid;
1,2,3,4-tetrahydro-6-sulfamoylcarbazole-2-carboxylic acid;
6-difluoromethylsulfonyl-1,2,3,4-tetrahydrocarbazole-2-carboxylic acid;
6-carbethoxy-1,2,3,4-tetrahydrocarbazole-2-carboxylic acid;
5-chloro-1,2,3,4-tetrahydro-6-sulfamylcarbazole-2-carboxylic acid;
6-chloro-9-(p-chlorobenzoyl)-1,2,3,4-tetrahydrocarbazole-2-carboxylic acid ethyl ester;
9-benzoyl-6-chloro-1,2,3,4-tetrahydrocarbazole-2-carboxylic acid;
6-dimethylsulfamoyl-1,2,3,4-tetrahydrocarbazole-2-carboxylic acid;
6-methylthio-1,2,3,4-tetrahydrocarbazole-2-carboxylic acid;
6-benzyloxy-1,2,3,4-tetrahydrocarbazole-2-carboxylic acid;
6-cyano-1,2,3,4-tetrahydrocarbazole-2-carboxylic acid;
6-carboxy-1,2,3,4-tetrahydrocarbazole-2-carboxylic acid;
6-ethyl-1,2,3,4-tetrahydrocarbazole-2-carboxylic acid;
6,7-methylenedioxy-1,2,3,4-tetrahydrocarbazole-2-carboxylic acid;
6-acetyl-1,2,3,4-tetrahydrocarbazole-2-carboxylic acid,
6-iodo-1,2,3,4-tetrahydrocarbazole-2-carboxylic acid;

6-chloro-1,2,3,4-tetrahydrocarbazole-2-carboxylic acid dimethylaminoethyl ester;
6,9-dimethyl-1,2,3,4-tetrahydrocarbazole-2-carboxylic acid;
6-chloro-1,2,3,4-tetrahydrocarbazole-2-carboxylic acid dimethylaminoethyl ester hydrochloride;
6-chloro-N,N-dimethyl-1,2,3,4-tetrahydrocarbazole-2-carboxamide;
6-methyl-1,2,3,4-tetrahydrocarbazole-2-carboxylic acid ethyl ester;
6-hydroxy-1,2,3,4-tetrahydrocarbazole-2-carboxylic acid; and the like.

Examples of compounds of this invention corresponding to formula I wherein n is 1 are:
7-chlorocyclopenta[b]indole-2-carboxylic acid;
7-chlorocyclopenta[b]indole-2-acetic acid;
7-chlorocyclopenta[b]indole-2-carboxylic acid ethyl ester;
7-methylcyclopenta[b]indole-2-carboxylic acid;
7-methoxycyclopenta[b]indole-2-carboxylic acid;
7-nitrocyclopenta[b]indole-2-carboxylic acid;
8-chlorocyclopenta[b]indole-2-carboxylic acid;
8-methylcyclopenta[b]indole-2-carboxylic acid;
7-fluorocyclopenta[b]indole-2-carboxylic acid;
7-bromocyclopenta[b]indole-2-carboxylic acid;
7-trifluoromethylcyclopenta[b]indole-2-carboxylic acid;
7-chloro-8-methylcyclopenta[b]indole-2-carboxylic acid;
7-chloro-6-methylcyclopenta[b]indole-2-carboxylic acid; and the like.

Preparation of compounds of formula I wherein *n* is 1 is exemplified by Reaction Scheme I:

SCHEME I

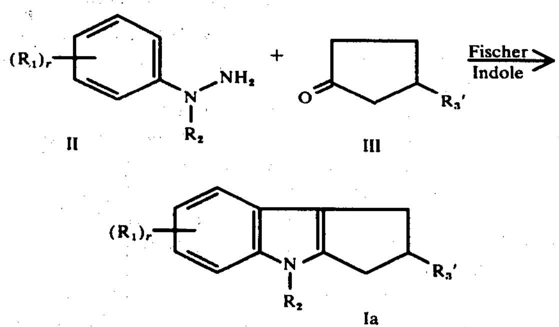

wherein $R_1$, $R_2$ and *r* are as previously described, and $R_3'$ is

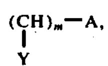

wherein A is cyano, hydroxy or lower alkoxy, Y is hydrogen or methyl, and *m* is 0–7, or

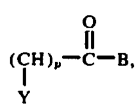

wherein B is hydroxy, carboxy, lower alkyl, lower alkoxy, amino, mono-lower alkylamino or di-lower alkylamino, Y is hydrogen or methyl, and *p* is 0–7.

In Reaction Scheme I, the reaction of the hydrazine of formula II with the cyalopentanone of formula III to yield the cyclopenta[b]indoles of formula Ia is carried out at a temperature in the range of about room temperature to about the reflux temperature of the reaction mixture; preferably, it is carried out at the reflux temperature of the reaction mixture. The reaction is effected in the presence of a solvent, for example, water, a lower alkanol such as methanol, ethanol or the like, acetic acid, formic acid, hexane, dioxane, benzene, toluene, dimethylformamide and the like, and an acidic condensing agent as used in the Fischer Indole synthesis, for example, hydrochloric acid, sulfuric acid, phosphoric acid, zinc chloride, copper chloride, boron trifluoride and the like, and various combinations thereof. Alternatively, the reaction of the hydrazine of formula II with the cyclopentanone of formula III can be effected by thermal cyclization with or without solvent. Conveniently, such cyclization is effected at an elevated temperature, for example, at a temperature in the range of from about 80° C. to about 200° C.

The separation of the desired cyclopenta[b]indole of formula Ia can be effected utilizing known techniques, for example, filtration, crystallization, distillation and the like.

The acids of formula Ia, i.e., the compounds of formula Ia, wherein B is hydroxy, and salts of such acids with bases, can be converted to a compound of formula I wherein B is amino-lower alkoxy, mono-lower alkylamino-lower alkoxy or di-lower alkylamino-lower alkoxy by known procedures. For example, a salt of an acid of forula I is reacted with an amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temperature at which the reaction is effected is not critical; conveniently, the reaction is carried out at a temperature in the range of from about room temperature and about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

Preparation of compounds of formula I wherein n is 2 is exemplified by Reaction Scheme II:

SCHEME II

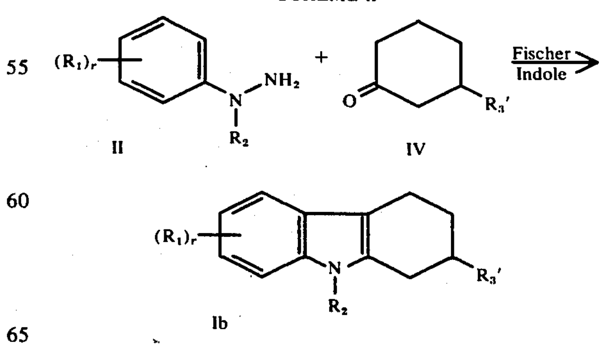

wherein $R_1$, $R_2$ and *r* are as previously described, and $R_3'$ is

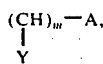

wherein A is cyano, hydroxy or lower alkoxy, Y is hydrogen or methyl, and *m* is 0-7, or

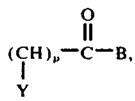

wherein B is hydroxy, carboxy, lower alkyl, lower alkoxy, amino, mono-lower alkylamino or di-lower alkylamino, Y is hydrogen or methyl, and *p* is 0–7.

In Reaction Scheme II, the reaction of the hydrazine of formula II with the cyclohexanone of formula IV to yield the corresponding 1,2,3,4-tetrahydrocarbazoles of formula Ib is carried out at a temperature in the range of from about room temperature to about the reflux temperature of the reaction mixture; preferably, it is carried out at the reflux temperature of the reaction mixture. The reaction is effected in the presence of a solvent, for example, water, a lower alkanol, such as methanol, ethanol or the like, acetic acid, formic acid, hexane, dioxane, benzene, toluene, dimethylformamide and the like, and an acidic condensing agent as used in the Fischer Indole synthesis, for example, hydrochloric acid, sulfuric acid, phosphoric acid, zinc chloride, copper chloride, boron trifluoride and the like, and various combinations thereof. Alternatively, the reaction of the hydrazine of formula II with the cyclohexanone of formula IV can be effected by thermal cyclization with or without solvent. Conveniently, such cyclization is effected at an elevated temperature, for example, at a temperature in the range of from about 80° C. to about 200° C.

The separation of the desired 1,2,3,4-tetrahydrocarbazole of formula Ib can be effected utilizing known techniques, for example, filtration, cyclization, distillation and the like.

The acids of formula Ib, i.e., the compounds of formula Ib, wherein B is hydroxy, and salts of such acids with bases, can be converted to a compound of formula I wherein B is amino-lower alkoxy mono-lower alkylamino-lower alkoxy or di-lower alkylamino-lower alkoxy by known procedures. For example, a salt of an acid of formula I is reacted with an amino-lower alkyl halide, mono-lower alkylamino-lower alkyl halide or di-lower alkylamino-lower alkyl halide, exemplary of which are aminoethyl chloride, methylamino-ethyl bromide, diethylaminomethyl chloride and the like, to yield the desired end product. The temprature at which the reaction is effected is not critical; conveniently, the reaction is carried out at a temperature in the range of from about room temperature and about the reflux temperature of the reaction mixture. Conveniently, the reaction can be carried out in a polar solvent, such as dimethylformamide, dimethylsulfoxide or the like. The molar ratio of reactants is not critical. Preferably, the reactants are utilized in a 1:1 molar ratio.

Exemplary of the compounds of formula II, utilized as reactants in the process of the invention, are:
p-chlorophenylhydrazine;
m-chlorophenylhydrazine;
o-chlorophenylhydrazine;
p-fluorophenylhydrazine;
p-bromophenylhydrazine;
3,4-dichlorophenylhydrazine;
p-trifluoromethylphenylhydrazine;
N-chloro-3-methylphenylhydrazine;
2,3-dichlorophenylhydrazine;
p-methylphenylhydrazine;
m-methylphenylhydrazine;
p-methoxyphenylhydrazine;
$N^1$-(4-chlorobenzyl)-p-chlorophenylhydrazine;
p-nitrophenylhydrazine;
1-methyl-1-phenylhydrazine;
p-sulfamidophenylhydrazine;
p-(difluoromethylsulfonyl)-phenylhydrazine;
p-carbethoxyphenylhydrazine; and
4-aminosulfonyl-3-chlorophenylhydrazine.

Exemplary of the compounds of formula III, utilized as reactants in the process of the invention, are:
cyclohexanone-3-carboxylic acid;
cyclohexanone-3-acetic acid; and
cyclohexanone-3-carboxylic acid ethyl ester.

Exemplary of the compounds of formula IV, utilized as reactants in the process of the invention, are:
cyclopentanone-3-carboxylic acid;
cyclopentanone-3-acetic acid; and
cyclopentanone-3-carboxylic acid ethyl ester.

The compounds of formula I when $R_1$ is amino, mono-lower alkylamino, di-lower alkylamino, and/or when B is amino-lower alkoxy, amino-lower alkylamino-lower alkoxy or di-lower alkylamino-lower alkoxy, form addition salts with pharmaceutically acceptable organic or inorganic acids such as hydrohalides, e.g., hydrochloride, hydrobromide, hydroiodide, other mineral acid salts such as sulfate, nitrate, phosphate and the like, alkyl- and mono-arylsulfonates such as ethanesulfonate, toluenesulfonate, benzenesulfonate, or the like, other organic acid salts such as acetate, tartrate, maleate, citrate, benzoate, salicylate, ascorbate and the like.

The compounds of formula I, when $R_1$ is carboxy and/or B is hydroxy or carboxy, form salts with pharmaceutically acceptable bases. Exemplary of such bases are alkali metal hydroxides, such as sodium hydroxide, potassium hydroxide, and the like; alkaline earth hydroxides, such as calcium hydroxide, barium hydroxide and the like; sodium alkoxides, such as sodium etholate, potassium etholate and the like; organic bases such as piperidine, diethanolamine, N-methylglucamine, and the like. Also included are the aluminum salts of the compounds of formula I, as above.

The compounds of formula I, including the salts of those compounds of formula I which form salts with pharmaceutically acceptable bases and acids, possess anti-inflammatory, analgesic and anti-rheumatic activity, and are therefore useful as anti-inflammatory, analgesic and anti-rheumatic agents. Their pharmacologically useful activities are demonstrated in warm-blooded animals using standard procedures.

For example, the anti-inflammatory activity activity is demonstrated in Albino rats of Hart Strain, weighing 125–155 gms. The test animals are given 10 mls. of vehicle[1], which contains the test compound per kg. of body weight. The animals are treated daily for 5 consecutive days. Three hours after the first treatment, 0.05 ml. of an 0.5 percent suspension of heat killed dessiccated *Mycobacterium butyricum* in U.S.P. olive oil, which has been steam sterilized for 30 minutes, is injected into the right hind foot of each rat. The paw volume is measured immediately after the injection of the adjuvant and again 96 hours later. The difference is recorded as volume of edema. The paw volume is measured by immersion of the paw into a column of mercury to an ink mark exactly at the level of the lateral malleolus. Percent inhibition is calculated by dividing the average control edema minus the average treatment edema by the average control edema times 100. The percent inhibition is plotted against dose on semilogarithmic probability paper and the dose required to produce a 30 percent reduction in edema is estimated therefrom and is expressed as $ED_{30}$.

[1]Hilgar, A. G. and Hummel, D. J.: Endocrine Bioassay Data, No. 1, p. 15, August 1965 (Cancer Chemotherapy National Service Center, N.I.H.)

When 6-chloro-1,2,3,4-tetrahydrocarbazole-2-carboxylic acid, which has demonstrated an $LD_{50}$ of, for example, 1120 mg. p.o. in mice, is utilized as the test substance at a dosage of 10 mg. p.o., an anti-inflammatory activity is observed ($ED_{30} = 10$).

The antipyretic activity of the compounds of the invention is demonstrated, for example, utilizing 30 male rats divided into six groups containing 5 rats/group. Control animals are given 1 cc/100 g. body weight of the vehicle. The test drug animals are given 200 mg/kg. of the drug in a concentration of 2 percent. Soluble and insoluble compounds are administered orally in aqueous suspended vehicle. One hour after administration of drug, these rats are injected with 0.1 ml. of a 2 percent suspension of Brewer's yeast beneath the plantar surface of the foot. Two hours after drug injections and 1 hour after the irritant, the temperatures of the inflammed foot, the normal foot and the rectum are recorded with the help of a thermocouple. Results are reported as degrees change from controls. The temperatures are averaged for the inflamed foot, the normal foot and the rectum. The averages for the treated groups are compared with the control averages and the results noted as degrees change from control.

When 6-chloro-1,2,3,4-tetrahydrocarbazole-2-carboxylic acid, which has demonstrated an $LD_{50}$ of, for example, 1120 mg. p.o. in mice, is utilized as the test substance at a dose of 200 mg/kg., an antipyretic activity is observed.

The analgesic activity of the compounds of the invention is demonstrated, for example, employing the method which is a modification of that described by Eddy (1950), Wolfe and MacDonald (1944) and Eddy and Leimbach (1952). The method determines the reaction time of mice dropped onto a hot plate maintained at 55±0.5° C. Six groups of male mice (5 mice/group) weighing between 20–30 grams are utilized. The initial reaction time of these mice is determined once, and the reaction time of each group is then averaged. The mice are then administered the vehicle and/or the compound to be tested by the oral, intraperitoneal or subcutaneous route. The average reaction time of each group is determined again at 30, 60 and 90 minutes after compound administration and is compared to controls. Reaction time is recorded as percent changes from control. All groups are averaged before and after treatment. A combined reaction time average (recorded as percent change of reaction time threshhold from controls) for all three periods is plotted against dose on graph paper, and a curve is drawn. The $ED_{50}$ is read from this curve.

When 6-chloro-1,2,3,4-tetrahydrocarbazole-2-carboxylic acid, which has demonstrated an $LD_{50}$ of, for example, 1120 mg. p.o. in mice, is utilized as the test substance at a dose ranging from 38 mg. to about 220 mg., analgesic activity is observed.

The compounds of formula I, their enantiomers and salts thereof as herein described, have effects qualitatively similar to those of phenylbutazone, known for its therapeutic uses and properties. Thus, the end products of this invention demonstrate a pattern of activity associated with anti-inflammatory agents of known efficacy and safety.

The compounds of formula I, their enantiomers and salts thereof as herein described, can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols, and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

Since the compounds of the invention possess asymmetric carbon atoms, they are ordinarily obtained as racemic mixtures. The resolution of such racemates into the optically active isomers can be carried out by known procedures. Some racemic mixtures can be precipitated as eutectics and can thereafter be separated. Chemical resolution is, however, preferred. By this method, diastereomers are formed from the racemic mixture with an optically active resolving agent, for example, an optically active base, such as d-α-(1-naphthyl)ethylamine, which can be reacted with the carboxyl group. The formed diastereomers are separated by selective crystallization and converted to the corresponding optical isomer. Thus, the invention covers the racemates of the compounds of formula I as well as their optically active isomers.

The following examples further illustrate the invention. All temperatures are in degrees centigrade, unless otherwise mentioned.

EXAMPLE 1

Preparation of 6-chloro-1,2,3,4-tetrahydrocarbazole-2-carboxylic acid

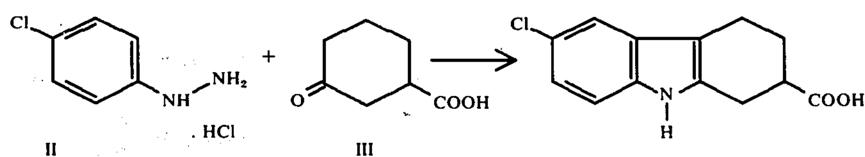

A mixture of 50 g. of p-chlorophenylhydrazine hydrochloride (formula II), 500 ml. of 80 percent acetic acid and 42 g. of cyclohexanone-3-carboxylic acid (formula III) was placed in a 1 liter round-bottomed, three-necked flask equipped with stirrer and reflux condenser. The mixture was stirred for 2 hours at room temperature under nitrogen and then heated to reflux. After stirring under reflux for 2.5 hours, the mixture was poured into a stirred mixture of 1 kg. of ice and 1 liter of water and stirred until the ice melted. Following filtration of the aqueous mixture, the filter cake was washed with water (4 × 100 ml.). Following removal of as much water as possible by filtration, the filter cake was placed in a vacuum oven and dried for 12 hours at 120° over sodium hydroxide pellets in vacuo. The dried filter cake (66 g.) was dissolved in 500 ml. of boiling ethanol, filtered through a heated funnel, and the filtrate concentrated to 400 ml. under a nitrogen atmosphere. When the solution cooled to room temperature, the mixture was set in a refrigerator at 5° C. for 72 hours to complete the crystallization. The crystalline product was collected by filtration and the filter cake was washed with cooled ethanol (2 × 30 ml.). There was obtained 40 g. (58 percent) of 6-chloro-1,2,3,4-tetrahydrocarbazole-2-carboxylic acid as a yellowish-tan powder which melted at 249°-250° when dried in vacuo over $P_2O_5$.

Concentration of the mother liquors in a Swisco under nitrogen to 150 ml. gave an additional 10.4 g. (m.p. 242°-246°). This second crop melted at 247°-248° when recrystallized from 80 ml. of ethanol.

In an analogous manner to Example 1, when the phenylhydrazine of formula II was replaced, as hereinafter set forth, the corresponding 1,2,3,4-tetrahydrocarbazole-2-carboxylic acids were obtained:

| | |
|---|---|
| Example 2 | Paramethylphenylhydrazine → 6-methyl-1,2,3,4-tetrahydrocarbazole-2-carboxylic acid, m.p. 254-255° (EtOAc) |
| Example 3 | Paramethoxyphenylhydrazine → 6-methoxy-1,2,3,4-tetrahydrocarbazole-2-carboxylic acid, m.p. 226-227° (EtOAc) |
| Example 4 | N'1-(4-chlorobenzyl)-paramethoxyphenylhydrazine → 9-(4-chlorobenzyl)-6-methoxy-1,2,3,4-tetrahydrocarbazole-2-carboxylic acid, m.p. 211.5-212° (EtOAc) |
| Example 5 | Paranitrophenylhydrazine → 6-nitro-1,2,3,4-tetrahydrocarbazole-2-carboxylic acid, m.p. 263-265° (EtOAc) |
| Example 6 | Metachlorophenylhydrazine → 7-chloro-1,2,3,4-tetrahydrocarbazole-2-carboxylic acid, m.p. 238-240° (EtOAc) |
| Example 7 | Metamethylphenylhydrazine → 7-methyl-1,2,3,4-tetrahydrocarbazole-2-carboxylic acid, m.p. 229-231° (EtOAc) |
| Example 8 | Orthochlorophenylhydrazine → 8-chloro-1,2,3,4-tetrahydrocarbazole-2-carboxylic acid, m.p. 189-190° (benzene) |
| Example 9 | Parafluorophenylhydrazine → 6-fluoro-1,2,3,4-tetrahydrocarbazole-2-carboxylic acid, m.p. 256-257° (EtOAc) |
| Example 10 | Parabromophenylhydrazine → 6-bromo-1,2,3,4-tetrahydrocarbazole-2-carboxylic acid, m.p. 229-230° (EtOAc) |
| Example 11 | 3,4-Dichlorophenylhydrazine → 6,7-dichloro-1,2,3,4-tetrahydrocarbazole-2-carboxylic acid, m.p. 309-310° (MeOH) |
| Example 12 | 3,4-Dichlorophenylhydrazine → 5,6-dichloro-1,2,3,4-tetrahydrocarbazole-2-carboxylic acid, m.p. 229-230° (benzene) |

The compound of Example 11 was separated from the compound of Example 12 by fractional crystallization of ethanol solutions of the mixture obtained in the reaction.

| | |
|---|---|
| Example 13 | Paratrifluoromethylphenylhydrazine → 6-trifluoromethyl-1,2,3,4-tetrahydrocarbazole-2-carboxylic acid, m.p. 233-234° (decomp.) (EtOAc) |
| Example 14 | 4-Chloro-3-methylphenylhydrazine → 6-chloro-7-methyl-1,2,3,4-tetrahydrocarbazole-2-carboxylic acid, m.p. 268-270° (MeOH) |
| Example 15 | 4-Chloro-3-methylphenylhydrazine → 6-chloro-5-methyl-1,2,3,4-tetrahydrocarbazole-2-carboxylic acid, m.p. 236-238° (benzene) |

The compound of Example 12 was separated from the compound of Example 15 by fractional crystallization of a methanol solution of the mixture of products obtained from the reaction.

| | |
|---|---|
| Example 16 | 1-Methyl-1-phenylhydrazine → 9-methyl-1,2,3,4-tetrahydrocarbazole-2-carboxylic acid, m.p. 228-229° (benzene) |
| Example 17 | 2,3-Dichlorophenylhydrazine → 7,8-dichloro-1,2,3,4-tetrahydrocarbazole-2-carboxylic acid, m.p. 217-218° (acetonitrile) |
| Example 18 | Parasulfamidophenylhydrazine → 1,2,3,4-tetrahydro-6-sulfamoylcarbazole-2-carboxylic acid, m.p. 293-294° (water) |
| Example 19 | Para-(difluoromethylsulfonyl)phenylhydrazine → 6-difluoromethylsulfonyl-1,2,3,4-tetrahydrocarbazole-2-carboxylic acid, m.p. 235-236° (EtOAc) |
| Example 20 | Paracarbethoxyphenylhydrazine → 6-carbethoxy-1,2,3,4-tetrahydrocarbazole-2-carboxylic acid, m.p. 222-223° (EtOAc) |
| Example 21 | 4-Aminosulfonyl-3-chlorophenylhydrazine → 5-chloro-1,2,3,4-tetrahydro-6-sulfamylcarbazole-2-carboxylic acid, m.p. 296-298° (EtOH) |
| Example 22 | Para-(dimethylsulfamoyl)phenylhydrazine → 6-dimethylsulfamoyl-1,2,3,4-tetrahydrocarbazole-2-carboxylic acid, m.p. 242-243° (EtOH) |
| Example 23 | Paramethylthiophenylhydrazine → 6-methylthio-1,2,3,4-tetrahydrocarbazole-2-carboxylic acid, m.p. 212-213° (EtOAc) |
| Example 24 | Parabenzyloxyphenylhydrazine → 6-benzyloxy-1,2,3,4-tetrahydrocarbazole-2-carboxylic acid, m.p. 225-227° (EtOAc) |
| Example 25 | Paracyanophenylhydrazine → 6-cyano-1,2,3,4-tetrahydrocarbazole-2-carboxylic acid, m.p. 302-305° (iso PrOH) |
| Example 26 | Paracarboxyphenylhydrazine → 6-carboxy-1,2,3,4-tetrahydrocarbazole-2-carboxylic acid, m.p. 327-329° (EtOH) |
| Example 27 | Paraethylphenylhydrazine → 6-ethyl-1,2,3,4-tetrahydrocarbazole-2-carboxylic |

-continued

| | |
|---|---|
| | acid, m.p. 231–232° (EtOAc) |
| Example 28 | 3,4-methylenedioxyphenylhydrazine ⟶ 6,7-methylenedioxy-1,2,3,4-tetrahydrocarbazole-2-carboxylic acid, m.p. 265–267° (EtOAc) |
| Example 29 | Paraacetylphenylhydrazine ⟶ 6-acetyl-1,2,3,4-tetrahydrocarbazole-2-carboxylic acid, m.p. 295–297° (EtOH) |
| Example 30 | Paraiodophenylhydrazine ⟶ 6-iodo-1,2,3,4-tetrahydrocarbazole-2-carboxylic acid, m.p. 178–179° ($EtOH,H_2O$) |

In an analogous manner to Example 1, when the cyclohexanone of formula II was replaced, as hereinafter set forth, the corresponding cyclopenta[b]indole or 1,2,3,4-tetrahydrocarbazole was obtained.

| | |
|---|---|
| Example 31 | Cyclopentanone-3-acetic acid ⟶ 7-chloro-cyclopenta[b]indole-2-acetic acid, m.p. 163–164° (EtOAc). Its piperidino salt has a melting point of 159–160° |
| Example 32 | Cyclopentanone-3-carboxylic acid ⟶ 7-chloro-cyclopenta[b]indole-2-carboxylic acid, m.p. 197–199° (EtOAc) |
| Example 33 | Cyclopentanone-3-carboxylic acid ethyl ester ⟶ 7-chlorocyclopenta[b]indole-2-carboxylic acid ethyl ester |
| Example 34 | Cyclohexanone-3-acetic acid ⟶ 6-chloro-1,2,3,4-tetrahydrocarbazole-2-acetic acid, m.p. 184–186° (benzene) |
| Example 35 | 3-cyclohexanone-α-methylacetic acid ⟶ 6-chloro-α-methyl-1,2,3,4-tetrahydrocarbazole-2-acetic acid (cis-trans isomers), m.p. 215–216° (EtOAc) |

EXAMPLE 36

Utilizing the procedure of Example 1, paramethylphenylhydrazine was reacted with cyclopentanone-3-carboxylic acid to give 7-methyl-cyclopenta[b]indole carboxylic acid, m.p. 250° (decomp.).

EXAMPLE 37

Preparation of 9-benzoyl-6-chloro-1,2,3,4-tetrahydrocarbazole-2-carboxylic acid A stirred mixture of 2.0 g. of $N^1$-p-chlorophenyl-$N^1$-benzoylhydrazine, 1.1 g. of cyclohexanone-3-carboxylic acid, 5 ml. of glacial acetic acid and 7 ml. of cyclohexane were heated under an atmosphere of nitrogen. After 3 hours of stirring at reflux, the reaction mixture was concentrated under reduced pressure and 10 ml. of ethanol was added to the residue. After standing overnight in the refrigerator, the insoluble portion was removed by filtration, washed with a small amount of cold ethanol and dried, yielding 0.4 g. of product, m.p. 196°–197°. Following a recrystallization from ethanol, 0.2 g. of 9-benzoyl-6-chloro-1,2,3,4-tetrahydrocarbazole-2-carboxylic acid was obtained, m.p. 207°–208°.

EXAMPLE 38

An alternate preparation of (±) 6-chloro-1,2,3,4-tetrahydrocarbazole-2-carboxylic acid A stirred mixture of 100 mg. of 9-benzoyl-6-chloro-1,2,3,4-tetrahydrocarbazole-2-carboxylic acid and 5 ml. of 3N sodium hydroxide was heated on a steam bath for 5 minutes and cooled to room temperature. After 1 hour at room temperature, the reaction mixture was further cooled in an ice bath, filtered and the filter cake was washed with 10 drops of cold water. The filter cake was dissolved in 20 ml. of warm water, and the resulting warm solution was made strongly acid with 1N hydrochloric acid. Following filtration, washing with warm water and drying, 56 mg. of (±) 6-chloro-1,2,3,4-tetrahydrocarbazole-2-carboxylic acid was obtained, m.p. 247°–249°.

EXAMPLE 39

Preparation of (+) 6-chloro-1,2,3,4-tetrahydrocarbazole-2-carboxylic acid

A solution of 8.8 g. (0.0515 mole) of 1-α-(1-naphthyl)ethylamine in 50 ml. of acetone was carefully added to a warm solution of 12.7 g. (0.051 mole) of (±) 6-chloro-1,2,3,4-tetrahydrocarbazole-2-carboxylic acid. After standing at room temperature for 48 hours, the mixture was filtered and the filter cake was washed with cold acetone, yielding 11.7 g. of a colorless salt, m.p. 188°–191°; $[\alpha]_D^{25}+2.4°$, which upon recrystallization from 100 ml. of acetone returned 4.8 g. of salt, m.p. 192°–193°; $[\alpha]_D^{25}+15.5°$. Upon two subsequent recrystallizations from acetone, 1.20 g., m.p. 196°–197°; $[\alpha]_D^{25}+31.1°$ was obtained. The salt (1.20 g.) was dissolved in warm acetone and after filtration, the solution was poured into a mixture of ice and hydrochloric acid. Following filtration and drying, 0.60 g. of product was obtained which gave, after crystallization from ethyl acetate, 0.45 g. of (+) 6-chloro-1,2,3,4-tetrahydrocarbazole-2-carboxylic acid, m.p. 249°–251°; $[\alpha]_D^{25}+59.7°$.

EXAMPLE 40

Preparation of (−) 6-chloro-1,2,3,4-tetrahydrocarbazole-2-carboxylic acid

A solution of 1.85 g. of d-α-(1-naphthyl)ethylamine in 30 ml. of acetone was carefully added to a solution of 2.7 g. of partially resolved 6-chloro-1,2,3,4-tetrahydrocarbazole-2-carboxylic acid ($[\alpha]_D^{25}-15.9°$, recovered from the filtrate of a previous resolution of the racemate). After standing for 3 days at room temperature, the mixture was filtered and the filter cake was washed with cold acetone, yielding 2.3 g., m.p. 191°–193°; $[\alpha]_D^{25}-17.2°$. Following two additional recrystallizations from acetone, 0.38 g. was obtained, m.p. 196°–197°; $[\alpha]_D^{25}-33.2°$. The salt (0.38 g.) was dissolved in warm acetone, and the resulting solution was poured onto a mixture of ice and hydrochloric acid. Following filtration and drying, 0.17 g. of product was obtained, which upon crystallization from ethyl acetate gave 0.098 g. of (−) 6-chloro-1,2,3,4-tetrahydrocarbazole-2-carboxylic acid, m.p. 249°–250°; $[\alpha]_D^{25}-63.0°$.

EXAMPLE 41

Preparation of 6-chloro-1,2,3,4-tetrahydrocarbazole-2-carboxylic acid methyl ester A mixture of 2 g. of 6-chloro-1,2,3,4-tetrahydrocarbazole-2-carboxylic acid and 40 ml. of methanol was heated to boiling on a steam bath. The solution was removed from the steam bath and three drops of concentrated sulfuric acid was added. The reaction was allowed to stand for 18 hours at room temperature and then cooled further for 2 hours in an ice bath. Following filtration, the filter cake was washed with cold methanol and air dried yielding 1.9 g. of 6-chloro-1,2,3,4-tetrahydrocarbazole-2-carboxylic acid methyl ester, m.p. 175°–176°.

EXAMPLE 42

Preparation of 6-chloro-1,2,3,4-tetrahydrocarbazole-2-carboxylic acid ethyl ester A solution of 2.8 g. of 6-chloro-1,2,3,4-tetrahydrocarbazole-2-carboxylic acid, 40 ml. of ethanol and 10 ml. of 7.5M ethanolic hydrogen chloride was allowed to remain at room temperature for 3 days. The solution was then concentrated to dryness under reduced pressure and the residue was partitioned between ether (200 ml.) and 3 percent sodium bicarbonate (200 ml.). The ether was separated and washed by extraction with water (2 × 100 ml.) and dried over anhydrous sodium sulfate. Following filtration of the desiccant, the ether was evaporated and the residue (2.9 g.) was recrystallized from ethanol to yield 2.4 g. of 6-chloro-1,2,3,4-tetrahydrocarbazole-2-carboxylic acid ethyl ester, melting at 141°–142°.

EXAMPLE 43

Preparation of 6-amino-1,2,3,4-tetrahydrocarbazole-2-carboxylic acid ethyl ester A mixture of 1.3 g. of 6-nitro-1,2,3,4-tetrahydrocarbazole-2-carboxylic acid ethyl ester, 0.5 teaspoonful of Raney nickel and 100 ml. of ethanol was shaken in a Parr hydrogenation apparatus under 3.7 atmospheres of hydrogen at room temperature. After 2 hours of shaking the uptake of hydrogen had stopped. The catalyst was removed by filtration and the filtrate was concentrated to dryness, yielding 1.2 g. of product. Following recrystallization from a mixture of hexane and ethyl acetate, a yield of 0.8 g. of 6-amino-1,2,3,4-tetrahydrocarbazole-2-carboxylic acid ethyl ester, m.p. 123°–124° was obtained.

EXAMPLE 44

Preparation of 9-acetyl-6-chloro-1,2,3,4-tetrahydrocarbazole-2-carboxylic acid ethyl ester A solution of 1.5 g. of 6-chloro-1,2,3,4-tetrahydrocarbazole-2-carboxylic acid ethyl ester, 20 ml. of chloroform, 2 ml. of acetic anhydride and 1 drop of concentrated sulfuric acid was stirred under reflux. After 7 hours the reaction mixture was poured onto ice (100 g.). When the ice melted, the mixture was extracted with chloroform (2 × 100 ml.). The chloroform phase was extracted with 5 percent sodium bicarbonate (2 × 50 ml.) and then extracted with water (2 × 100 ml.).

Following drying of the chloroform solution over anhydrous sodium sulfate, the desiccant was removed by filtration and the chloroform evaporated under reduced pressure yielding 1.0 g. of product. Upon recrystallization from ethanol, 0.5 g. of 9-acetyl-6-chloro-1,2,3,4-tetrahydrocarbazole-2-carboxylic acid ethyl ester, m.p. 95°–96° was obtained.

EXAMPLE 45

Preparation of 6-dimethylamino-1,2,3,4-tetrahydrocarbazole-2-carboxylic acid ethyl ester A mixture of 3 g. of 6-nitro-1,2,3,4-tetrahydrocarbazole-2-carboxylic acid ethyl ester, 100 ml. of methanol, 2.1 g. of 37 percent aqueous formaldehyde and 0.5 teaspoonful of Raney nickel was shaken in a Parr hydrogenation apparatus under 3.7 atmospheres of hydrogen at room temperature. After 4 hours of shaking, the uptake of hydrogen had stopped. The catalyst was removed by filtration, and the filtrate was concentrated to dryness, yielding 2.8 g. of product. Recrystallization from ethyl acetate gave 1.7 g. of 6-dimethylamino-1,2,3,4-tetrahydrocarbazole-2-carboxylic acid ethyl ester, m.p. 100°–101°.

EXAMPLE 46

Preparation of 6-chloro-9-methyl-1,2,3,4-tetrahydrocarbazole-2-carboxylic acid

A mixture of 4.6 g. of 6-chloro-9-methyl-1,2,3,4-tetrahydrocarbazole-2-carboxylic acid ethyl ester, 25 ml. of ethanol and 25 ml. of 3N sodium hydroxide was refluxed and stirred for 6 hours. Upon cooling to room temperature, the reaction mixture was concentrated to dryness under reduced pressure. The residue was dissolved in water (300 ml.) and filtered. The filter cake was washed with water (4 × 50 ml.) and dried, yielding 4.2 g. of product, m.p. 259°–260°. Upon recrystallization from ethyl acetate, 4.0. g. of 6-chloro-9-methyl-1,2,3,4-tetrahydrocarbazole-2-carboxylic acid was obtained, m.p. 259°–260°.

EXAMPLE 47

Preparation of 6-chloro-9-methyl-1,2,3,4-tetrahydrocarbazole-2-carboxylic acid ethyl ester A mixture of 1.3 g. of 55 percent sodium hydride in mineral oil, 8 g. of 6-chloro-1,2,3,4-tetrahydrocarbazole-2-carboxylic acid ethyl ester and 50 ml. of dimethylformamide was stirred at room temperature. After 1.5 hours all the sodium hydride had reacted and a solution of 4.5 g. of methyl iodide in 15 ml. of dimethylformamide was added. The mixture was stirred for 6 hours between 60°–65° C. Upon cooling to room temperature, the reaction mixture was concentrated to dryness under reduced pressure and the residue was partitioned between ether (200 ml.) and water (200 ml.). The ether phase was separated and washed by extraction with water (2 × 100 ml.). After the ether solution had dried over sodium sulfate, the desiccant was removed by filtration and the ether evaporated, yielding 7.2 g. of product. Following crystallization from methanol, 4.6 g. of 6-chloro-9-methyl-1,2,3,4-tetrahydrocarbazole-2-carboxylic acid ethyl ester was obtained, m.p. 126°–127°.

EXAMPLE 48

Preparation of 6-chloro-1,2,3,4-tetrahydrocarbazole-2-methanol

To a stirred mixture of 1.3 g. of lithium aluminum hydride in 90 ml. of dry ether (under an atmospheric dry nitrogen) was added 3 g. of powdered 6-chloro-1,2,3,4-tetrahydrocarbazole-2-carboxylic acid ethyl ester. Following the addition, the mixture was stirred under reflux for 7 hours and then cooled (10°) in an ice bath. 10 ml. of water was then added dropwise. The mixture was stirred ½ hour at room temperature and filtered. The filter cake was washed with ether (3 × 50 ml.) and the combined filtrate and washings were dried over anhydrous sodium sulfate. Following filtration of the desiccant and evaporation of the ether solution, 2.3 g. of residue was obtained. Crystallization from ethyl acetate gave 1.4 g. of 6-chloro-1,2,3,4-tetrahydrocarbazole-2-methanol, m.p. 168°–169°.

EXAMPLE 49

Preparation of 6-chloro-9-(p-chlorobenzoyl)-1,2,3,4-tetrahydrocarbazole-2-carboxylic acid ethyl ester To a stirred solution of 5.5 g. of 6-chloro-1,2,3,4-tetrahydrocarbazole-2-carboxylic acid ethyl ester in 40 ml. of dimethylformamide was added 0.9 g. of 54.5 percent sodium hydride in mineral oil. After the mixture had stirred 1 hour at room temperature, 3.5 g. of p-chlorobenzoyl chloride in 10 ml. of dimethylformamide was added dropwise over the course of 10 minutes. The mixture was then stirred for 5 hours between 60°–70° and then poured onto ice (500 g.). The mixture was extracted with ether (3 × 150 ml.) and the ether was in turn extracted with water (5 × 100 ml.). After drying the ether solution over sodium sulfate, the desiccant was removed by filtration and the ether was evaporated. Upon recrystallization of the residue with ethyl acetate, 3.8 g. of product was obtained, m.p. 129°–132°. Following two further recrystallizations from methanol, a yield of 2.3 g. of 6-chloro-9-(p-chlorobenzoyl)-1,2,3,4-tetrahydrocarbazole-2-carboxylic acid ethyl ester was obtained, m.p. 136°–137°.

EXAMPLE 50

Preparation of 6-chloro-1,2,3,4-tetrahydrocarbazole-2-carboxylic acid amide

A mixture of 2.5 g. of methyl-6-chloro-1,2,3,4-tetrahydrocarbazole-2-carboxylate, 20 g. of liquid ammonia and 150 ml. of methanol was placed in a pressure bottle. The mixture was shaken at 60° for 40 hours (internal pressure 60 lb/in$^2$). Upon cooling to room temperature, the mixture was concentrated to dryness yielding 2.1 g. of product. Following a crystallization from ethyl acetate, 0.8 g. of 6-chloro-1,2,3,4-tetrahydrocarbazole-2-carboxylic acid amide was obtained, m.p. 203°–204°.

EXAMPLE 51

Preparation of the piperidine salt of 6-chloro-1,2,3,4-tetrahydrocarbazole-2-carboxylic acid The procedure of Example 1 was repeated to the point of obtaining the dried filter cake which was dissolved in 700 ml. of warm acetone (45°). The resulting solution was cooled to 20° C. with an ice bath. A solution of 23 g. of piperidine in 100 ml. of acetone was then added with constant stirring to the solution of the filter cake, keeping the temperature below 25°. The precipitated piperidine salt was allowed to remain in the ice bath for two hours to complete the crystallization and then filtered. The filter cake was washed with chilled acetone (6 × 50 ml.) and air dried for 24 hours. There was obtained 91.6 g. (98 percent) of a colorless crystalline piperidine salt of 6-chloro-1,2,3,4-tetrahydrocarbazole-2-carboxylic acid, melting at 197°–205° after sintering at 194°.

EXAMPLE 52

Preparation of 6-chloro-2-cyano-1,2,3,4-tetrahydrocarbazole

A suspension of 5 g. of 6-chloro-1,2,3,4-tetrahydrocarbazole-2-carboxamide in 50 ml. of phosphorus oxychloride was cooled in an ice water bath. After the addition of 5 ml. of triethylamine, the reaction mixture was heated for 1-½ hours on a steam bath. The reaction mixture was then evaporated to dryness, and the residue was partitioned between 150 ml. of methylene chloride and 50 ml. of water. The aqueous phase was extracted twice with 50 ml. portions of methylene chloride. The combined organic extracts were evaporated to dryness, dried over sodium sulfate and filtered through 50 g. of alumina Woelm activity II. Evaporation of the eluates to dryness gave 4.8 g. (98 percent) of 6-chloro-2-cyano-1,2,3,4-tetrahydrocarbazole, m.p. 181°–182°.

EXAMPLE 53

Preparation of 2-acetyl-6-chloro-1,2,3,4-tetrahydrocarbazole

A solution of 1.0 g. of 6-chloro-2-cyano-1,2,3,4-tetrahydrocarbazole in 15 ml. of tetrahydrofuran was added dropwise to a cooled (10° C.), stirred solution of 9.6 g. of methyl magnesium iodide in 20 ml. of ether. The reaction mixture was refluxed and stirred under an atmosphere of dry nitrogen for 24 hours. Thereafter, it was cooled to 5° C. in an ice bath and 50 ml. of cold water was carefully added followed by 3 ml. of concentrated hydrochloric acid. The mixture was heated for 3 hours on a steam bath. After the mixture had been cooled by adding ice, it was extracted with ether. The ether solution was washed by extraction with dilute sodium bicarbonate and water. When the ether solution had dried over anhydrous magnesium sulfate, the desiccant was removed by filtration and the ether was removed by distillation, yielding 0.8 g.of product. Following crystallization from a mixture of hexane and ethyl acetate, 0.4 g. of 2-acetyl-6-chloro-1,2,3,4-tetrahydrocarbazole was obtained, m.p. 159°–161°.

EXAMPLE 54

Preparation of 6-chloro-1,2,3,4-tetrahydrocarbazole-2-carboxylic acid dimethylaminoethyl ester A solution of 3.0 g. of dimethylaminoethylchloride in 10 ml. of dimethylformamide was added dropwise to a stirred solution of 6-chloro-1,2,3,4-tetrahydrocarbazole-2-carboxylic acid sodium salt (made from 4 g. of 6-chloro-1,2,3,4-tetrahydrocarbazole-2-carboxylic acid, 0.71 g. of 54.5 percent sodium hydride dispersion in mineral oil and 40 ml. of dimethylformamide). After the addition, the stirred mixture was heated to 70° C. and held at that temperature for 4 hours. Upon cooling to room temperature, the reaction mixture was poured into a mixture of ice and water and extracted with ether. The ether extracted was washed by extraction with water, separated, and dried over anhydrous sodium sulfate. Following filtration of the desiccant and evaporation of the ether, a yield of 5 g. was obtained. Crystallization from acetone gave 3.1 g. of 6-chloro-1,2,3,4,-tetrahydrocarbazole-2-carboxylic acid dimethylaminoethyl ester, m.p. 123°–124°.

EXAMPLE 55

Preparation of 6,9-dimethyl-1,2,3,4-tetrahydrocarbazole-2-carboxylic acid

A solution of 6 g. of 6-methyl-1,2,3,4-tetrahydrocarbazole-2-carboxylic acid ethyl ester in 20 ml. of dimethylformamide was added to a stirred mixture of 1.1 g. of NaH (55 percent suspension in mineral oil) in 10 ml. of dimethylformamide. After the mixture had stirred for 1 hour at room temperature, a solution of 4 g. of methyliodide in 10 ml. of dimethylformamide was added dropwise. Following the last addition, the reaction mixture was stirred and heated (40°) for 7 hours. Upon cooling to room temperature, the reaction mixture was poured onto ice and the mixture extracted with ether. The ether solution was washed with water and dried over anhydrous sodium sulfate. Following filtration of the desiccant and evaporation of the ether, a yield of 6.3 g. was obtained. Crystallization from methanol yielded 1.2 g. of 6,9-dimethyl-1,2,3,4-tetrahydrocarbazole-2-carboxylic acid ethyl ester, m.p. 84°–85°, which was dissolved in 10 ml. of ethanol and 10 ml. 3N sodium hydroxide was added. The solution was refluxed and stirred for 4 hours and concentrated to dryness on an evaporator. The residue was dissolved in 300 ml. of warm water and filtered through a celite filter bed. The filtrate was made acid and the resulting precipitate was filtered and washed with water. After drying, a yield of 1.0 g. was obtained. Crystallization from ethyl acetate afforded 0.6 g. of 6,9-dimethyl-1,2,3,4-tetrahydrocarbazole-2-carboxylic acid, m.p. 240°–242°.

EXAMPLE 56

Preparation of 6-chloro-1,2,3,4-tetrahydrocarbazole-2-carboxylic acid dimethylaminoethyl ester hydrochloride A slight excess of 7.5N alcoholic hydrogen chloride was added to a solution of 2.7 g. of 6-chloro-1,2,3,4-tetrahydrocarbazole-2-carboxylic acid dimethylaminoethyl ester in 15 ml. of ethanol. Ether was added until crystallization was induced and the resulting precipitate was filtered and washed with a mixture of ethanol and ether. Upon drying, 2.8 g. of the salt, 6-chloro-1,2,3,4-tetrahydrocarbazole-2-carboxylic acid dimethylaminoethyl ester hydrochloride, m.p. 201°–203°, was obtained.

EXAMPLE 57

Preparation of 6-chloro-N,N-dimethyl-1,2,3,4-tetrahydrocarbazole-2-carboxamide Under an atmosphere of nitrogen, 10 g. of 6-chloro-1,2,3,4-tetrahydrocarbazole-2-carboxylic acid dimethyl amine salt was stirred and heated (230°–250°) for 7 hours. When the reaction mixture had cooled to room temperature, it was partitioned between chloroform and dilute sodium hydroxide. The chloroform layer was separated and washed with water. After drying over anhydrous sodium sulfate, the desiccant was removed by filtration and the chloroform evaporated, yielding 4.2 g. Crystallization from ethyl acetate afforded 1.0 g. of 6-chloro-N,N-dimethyl-1,2,3,4-tetrahydrocarbazole-2-carboxamide, m.p. 176°–177°.

EXAMPLE 58

Preparation of 6-methyl-1,2,3,4-tetrahydrocarbazole-2-carboxylic acid ethyl ester 6-Methyl-1,2,3,4-tetrahydrocarbazole-2-carboxylic acid (10 g.) was dissolved in 300 ml. of warm ethanol and 5 ml. of 7N alcoholic hydrogen chloride was added. The solution was thoroughly mixed and allowed to remain at room temperature for 2 days. After cooling in an ice bath for 5 hours, the mixture was filtered and washed with several volumes of ethanol. Upon drying, a yield of 7.3 g. of 6-methyl-1,2,3,4-tetrahydrocarbazole-2-carboxylic acid ethyl ester, m.p. 117°–118°, was obtained.

EXAMPLE 59

Preparation of 6-hydroxy-1,2,3,4-tetrahydrocarbazole-2-carboxylic acid

A mixture of 3 g. of 6-benzyloxy-1,2,3,4-tetrahydrocarbazole-2-carboxylic acid, 100 ml. of ethanol, 0.5 g. of 10 percent palladium on carbon and 20 ml. of water was shaken under an atmosphere of hydrogen (56 p.s.i.) at room temperature. After 4 hours of shaking, the hydrogen uptake had stopped and the reduction was terminated. The catalyst was removed by filtration, and the filtrate was concentrated under reduced pressure, yielding 2.8 g. Crystallization from ethyl acetate gave 1.4 g. of 6-hydroxy-1,2,3,4-tetrahydrocarbazole-2-carboxylic acid, m.p. 255°–257°.

EXAMPLE 60

6-Chloro-1,2,3,4-tetrahydrocarbazole-2-carboxylic acid

| Suppository Formulation | Per 1.3 Gm. Suppository |
|---|---|
| 6-chloro-1,2,3,4-tetrahydrocarbazole-2-carboxylic acid | 0.025 gm. |
| Wecobee M* | 1.230 gm. |

-continued

| Suppository Formulation | Per 1.3 Gm. Suppository |
|---|---|
| Carnauba Wax | 0.045 gm. |

*E. F. Drew Company, 522 Fifth Avenue, New York, N.Y.

Procedure:

1. The Wecobee M and the carnauba wax were melted in a suitable size glass lined container (stainless steel may also be used), mixed well and cooled to 45° C.

2. 6-chloro-1,2,3,4-tetrahydrocarbazole-2-carboxylic acid, which had been reduced to a fine powder with no lumps, was added and stirred until completely and uniformly dispersed.

3. The mixture was poured into suppository molds to yield suppositories having an individual weight of 1.3 gms.

4. The suppositories were cooled and removed from molds. They were individually wrapped in wax paper for packaging. (Foil may also be used).

EXAMPLE 61

6-chloro-1,2,3,4-tetrahydrocarbazole-2-carboxylic acid

| Tablet Formulation | Per Tablet |
|---|---|
| 6-chloro-1,2,3,4-tetrahydrocarbazole-2-carboxylic acid | 25.00 mg. |
| Lactose, U.S.P. | 64.50 mg. |
| Corn Starch | 10.00 mg. |
| Magnesium Stearate | 0.50 mg. |

Procedure:

1. 6-chloro-1,2,3,4-tetrahydrocarbazole-2-carboxylic acid was mixed with the lactose, corn starch and magnesium stearate in a suitable mixer.

2. The mixture was further blended by passing through a Fitzpatrick Comminuting Machine fitted with a No. 1A screen with knives forward.

3. The mixed powders were slugged on a tablet compressing machine.

4. The slugs were comminuted to a suitable mesh size (No. 16 screen) and mixed well.

5. The tablets were compressed at a tablet weight of 100 mg. using tablet punches having a diameter of approximately ¼ inch. (Tablets may be either flat or biconvex and may be scored if desired.)

EXAMPLE 62

6-chloro-1,2,3,4-tetrahydrocarbazole-2-carboxylic acid

| Capsule Formulation | Per Capsule |
|---|---|
| 6-chloro-1,2,3,4-tetrahydrocarbazole-2-carboxylic acid | 50 mg. |
| Lactose, U.S.P. | 125 mg. |
| Corn Starch, U.S.P. | 30 mg. |
| Talc, U.S.P. | 5 mg. |
| Total Weight | 210 mg. |

Procedure:

1. 6-chloro-1,2,3,4-tetrahydrocarbazole-2-carboxylic acid was mixed with lactose and corn starch in a suitable mixer.

2. The mixture was further blended by passing through a Fitzpatrick Comminuting Machine with a No. 1A screen with knives forward.

3. The blended powder was returned to the mixer, the talc added and blended thoroughly.

4. The mixture was filled into No. 4 hard shell gelatin capsules on a Parke Davis capsulating machine.

EXAMPLE 63

6-chloro-1,2,3,4-tetrahydrocarbazole-2-carboxylic acid

| Parenteral Formulation<br>Each 1 cc. ampul contains: | Per cc.: |
|---|---|
| 6-chloro-1,2,3,4-tetrahydrocarbazole-2-carboxylic acid | 10.2 mg. (2% excess) |
| Methyl Paraben, U.S.P. | 1.8 mg. |
| Propyl Paraben, U.S.P. | 0.2 mg. |
| Sodium Hydroxide, U.S.P. q.s. ph | 8.0 |
| Water for Injection, U.S.P. q.s. ad | 1 cc. |

Procedure (For 10,000 cc.):

1. In a clean glass or glass-lined vessel, 8,000 cc. of Water for Injection were heated to 90° C. It was then cooled to 50°–60° C. and 18 gms. of methyl paraben and 2 gms. of propyl paraben were added and dissolved with stirring. The solution was then allowed to cool to room temperature.

2. The 102.0 gms. of 6-chloro-1,2,3,4-tetrahydrocarbazole-2-carboxylic acid were added under an atmosphere of nitrogen and stirred until completely dispersed.

3. The sodium hydroxide was added as a 10% solution until the pH was adjusted to 8.0 plus or minus 0.2, and the drug was completely dissolved.

4. Sufficient water for injection was then added to make a total volume of 10,000 cc.

5. This solution was then filtered through an 02 Selas candle, filled into suitable size ampuls, gassed with nitrogen and sealed. It was autoclaved at 10 lbs. PSI for 30 minutes.

We claim:

1. 7-chloro-cyclopenta[bindole-2-carboxylic acid or a salt thereof with a pharmaceutically acceptable base.

2. 7-chloro-cyclopenta[b]indole-2-carboxylic acid ethyl ester.

* * * * *

UNITED STATES PATENT AND TRADEMARK OFFICE

CERTIFICATE OF CORRECTION

PATENT NO. : 4,009,181

DATED : February 22, 1977

INVENTOR(S) : Leo Berger et al.

It is certified that error appears in the above-identified patent and that said Letters Patent are hereby corrected as shown below:

Column 22, claim 1, line 61 "-cyclopenta[bindole-" should be:

-cyclopenta[b] indole-

Signed and Sealed this

*twenty-third* Day of *August 1977*

[SEAL]

*Attest:*

RUTH C. MASON
*Attesting Officer*

C. MARSHALL DANN
*Commissioner of Patents and Trademarks*